United States Patent
Wake (10) Patent No.: US 9,138,283 B2
(45) Date of Patent: Sep. 22, 2015

(54) HIGH-FREQUENCY KNIFE

(71) Applicant: OLYMPUS MEDICAL SYSTEMS CORP., Shibuya-ku, Tokyo (JP)

(72) Inventor: Fuminori Wake, Tokyo (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 67 days.

(21) Appl. No.: 14/157,045

(22) Filed: Jan. 16, 2014

(65) Prior Publication Data

US 2014/0207134 A1 Jul. 24, 2014

Related U.S. Application Data

(63) Continuation of application No. PCT/JP2013/073690, filed on Sep. 3, 2013.

(30) Foreign Application Priority Data

Sep. 12, 2012 (JP) ................. 2012-200649

(51) Int. Cl.
*A61B 18/12* (2006.01)
*A61B 18/14* (2006.01)
*A61B 18/00* (2006.01)

(52) U.S. Cl.
CPC ............. *A61B 18/14* (2013.01); *A61B 18/1492* (2013.01); *A61B 2018/0016* (2013.01); *A61B 2018/00494* (2013.01); *A61B 2018/144* (2013.01); *A61B 2018/1412* (2013.01); *A61B 2018/1475* (2013.01)

(58) Field of Classification Search
CPC ............... A61B 18/14; A61B 18/1492; A61B 2018/0016; A61B 2018/00494; A61B 2018/1412; A61B 2018/144; A61B 2018/1475
See application file for complete search history.

(56) References Cited

U.S. PATENT DOCUMENTS

| | | |
|---|---|---|
| 2004/0210215 A1 | 10/2004 | Okada |
| 2005/0072280 A1 | 4/2005 | Ono et al. |
| 2012/0035607 A1 | 2/2012 | Karwei |

FOREIGN PATENT DOCUMENTS

| | | |
|---|---|---|
| JP | A-2004-167081 | 6/2004 |
| JP | A-2005-110861 | 4/2005 |
| JP | B2-4455002 | 4/2010 |
| JP | A-2012-75657 | 4/2012 |
| JP | A-2012-523863 | 10/2012 |

OTHER PUBLICATIONS

Jul. 29, 2014 Office Action issued in Japanese Application No. 2014-505449 (with translation).
International Search Report issued in International Application No. PCT/JP2013/073690 on Oct. 22, 2013 (with translation).

*Primary Examiner* — Michael Peffley
*Assistant Examiner* — Daniel Fowler
(74) *Attorney, Agent, or Firm* — Oliff PLC (57) ABSTRACT

In a high-frequency knife, a through hole that extends in the direction of an axis is formed on a radial outer side of a second electrode in a larger-diameter portion, and a distance increasing portion increases a creeping distance along an external surface of the larger-diameter portion between an outer peripheral surface of the second electrode exposed to the outside and an opening of the through hole on a proximal end side.

2 Claims, 10 Drawing Sheets

HIGH-FREQUENCY KNIFE

TECHNICAL BACKGROUND

1. Field of the Invention

The present invention relates to a high-frequency knife for incising a living body tissue or the like.

This application is a continuation claiming priority on the basis of Japanese Patent Application No. 2012/200649 filed in Japan on Sep. 12, 2012 and based on PCT/JP2013/073690 filed on Sep. 3, 2013. The contents of both the Japanese Patent Application and the PCT Application are incorporated herein by reference.

2. Background Art

In the related art, the treatment of endoscopically incising living body tissues, such as a mucous membrane, is performed. In order to perform such incision treatment, for example, a high-frequency knife described in Japanese Patent No. 4455002 is known.

In this high-frequency knife, a stopper member is coupled to a tip of a sheath. A ring-like insulated tip (supporting member) is disposed on a distal end side of the stopper member. A proximal end portion of a knife portion (electrode portion) is connected to a distal end portion of an operating wire, which is inserted through the inside of the sheath, via a stopper receiving portion. This knife portion includes an electrode having a proximal end portion connected to the stopper receiving portion, and an electrical insulator portion (a larger-diameter portion) provided at a distal end portion of the electrode.

The electrode includes a first electrode portion (a rod-shaped electrode or a tubular electrode) that is formed as a small diameter rod with a constant diameter, and a second electrode portion (auxiliary electrode) that is provided at a distal end portion of the first electrode portion, and radially extends in the radial direction of the first electrode portion. The electrode is formed from a conductive material, such as a titanium alloy.

In the high-frequency knife configured in this way, if the operating wire is moved (pulled back) to the proximal end side with respect to the sheath, the second electrode portion abuts against the insulated tip. This is a state where the knife portion is not used. On the other hand, if the operating wire is moved (pushed in) to the distal end side with respect to the sheath, the second electrode portion advances to separate from the distal end of the sheath. This state is a state where the knife portion is used, such as a case where a tissue, such as a mucous membrane is excised by applying an electric current to the knife portion.

When the excision of the mucous membrane is performed using the high-frequency knife, a saline is injected into a submucosal layer of a lesioned mucous membrane portion to be excised, using an injection needle, and the lesioned mucous membrane portion is made to bulge. A counter electrode plate is worn by a patient. The knife portion of the high-frequency knife is inserted into a hole made around the lesioned mucous membrane portion, in a state where the second electrode portion is separated from the distal end of the sheath. If the knife portion is moved in a transverse direction (a radial direction orthogonal to the direction of an axis of the sheath) while supplying a high frequency current to the electrode of the knife portion, the mucous membrane that comes into contact with the first electrode portion is incised.

The knife portion to which the high frequency current is supplied has a high temperature of, for example, hundreds of degrees Celsius.

When the mucous membrane is excised, blood may flow out of an excised portion or the like. The study for cleansing this blood, which has flowed out, with the aforementioned high-frequency knife is also performed. That is, a gap is formed between the insulated tip and the operating wire, and a guide hole is formed in the electrical insulator portion so as to extend in the axis direction. This guide hole is formed between the second electrode portions that are adjacent to each other in the radial direction when viewed in the axis direction.

Then, if the saline is made to flow into a conduit line of the sheath in a state where the operating wire is pulled back and the second electrode portions are made to abut against the insulated tip, the saline is jetted to the front of the electrical insulator portion through the aforementioned gap and guide hole.

SUMMARY OF THE INVENTION

A high-frequency knife related to a first aspect of the invention includes a sheath which has electric insulation and flexibility, has a conduit line formed therein and extends in an axis direction, an operating wire which is inserted through the conduit line so as to be capable of advancing and retracting in the axis direction; and an electrode portion which is provided at a distal end portion of the operating wire, wherein the electrode portion includes: a first electrode which is rod-shaped, extends in the axis direction, is inserted through the conduit line, and has a proximal end portion electrically connected to the operating wire; a larger-diameter portion which is provided at a distal end portion of the first electrode, has electric insulation, and has a larger external diameter than an external diameter of the first electrode; a second electrode which is formed so as to surround the first electrode from a proximal end surface of the larger-diameter portion, and is electrically connected to the first electrode; and a distance increasing portion which is provided at the proximal end surface of the larger-diameter portion. A through hole that extends in the axis direction is formed on a radial outer side of the second electrode in the larger-diameter portion, and the distance increasing portion increases a creeping distance along an external surface of the larger-diameter portion between an outer peripheral surface of the second electrode exposed to an outside and an opening of a proximal end side of the through hole.

According to a second aspect of the present invention, in the high-frequency knife of the aforementioned first aspect, the distance increasing portion may be formed from a material having electric insulation and is provided so as to protrude from the proximal end surface of the larger-diameter portion toward a proximal end side of the high-frequency knife, and the opening of the through hole is formed in a proximal end surface of the distance increasing portion protruding to the proximal end side.

According to a third aspect of the present invention, in the high-frequency knife of the aforementioned second aspect, the proximal end surface of the distance increasing portion may be provided so as to coincide with a proximal end surface of the electrode in the axis direction.

According to a fourth aspect of the present invention, in the high-frequency knife of the aforementioned first aspect, the distance increasing portion may be provided at a position between the electrode and the opening of the through hole when viewed in the axis direction so as to be recessed from the proximal end surface of the larger-diameter portion toward a distal end side of the high-frequency knife.

According to a fifth aspect of the present invention, in the high-frequency knife of the aforementioned first aspect, the distance increasing portion may be provided at a position that overlaps the opening of the through hole when viewed in the axis direction so as to be recessed from the proximal end surface of the larger-diameter portion toward a distal end side of the high-frequency knife, and the opening of the through hole may be formed in a bottom surface of the distance increasing portion that is recessed from the proximal end surface of the larger-diameter portion toward the distal end side of the high-frequency knife.

According to a sixth aspect of the present invention, in the high-frequency knife of any one of the first to fifth aspects, the electrode portion may have a plurality of auxiliary electrodes that extend radially outward from the outer peripheral surface of the second electrode, and when viewed in the axis direction, the through hole of the larger-diameter portion may be formed between the auxiliary electrodes that are adjacent to each other around an axis.

PREFERRED EMBODIMENTS

Hereinafter, an embodiment of a high-frequency knife related to the invention is described, referring to FIGS. 1 to 20.

Figure 1:
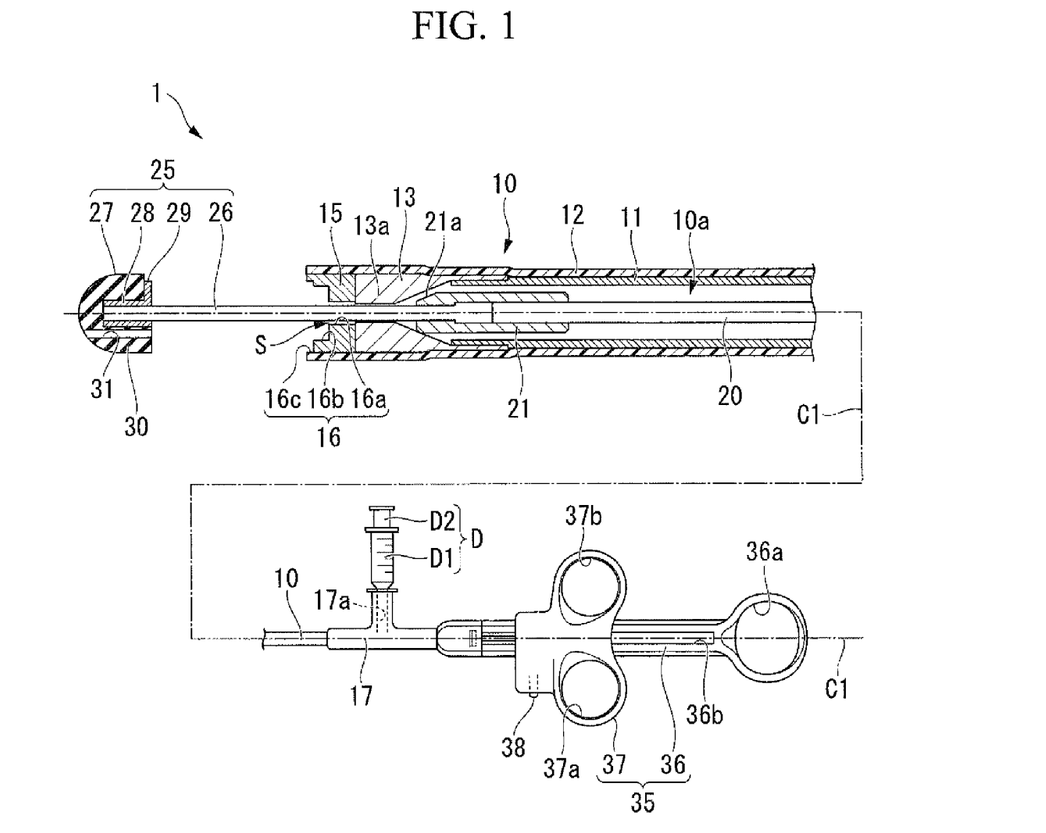
FIG. 1 is a partially broken side view when a high-frequency knife of an embodiment of the invention is brought into a push-in state.

As shown in FIG. 1, the high-frequency knife 1 of the present embodiment includes a sheath 10 that has a conduit line formed therein, an insulated tip (supporting member) 15 that is provided on an inner peripheral surface of a distal end portion of the sheath 10, an operating wire 20 that is provided in the conduit line of the sheath 10 and is advanceably and retractably inserted in the direction of an axis C1 of the sheath 10, and an electrode portion 25 that is provided at a distal end portion of the operating wire 20.

In the following, a side in which an electrode portion 25 relative to the operating wire 20 is provided is referred to as a distal end side and a side in which the operating wire 20 relative to the electrode portion 25 is provided is referred to as a proximal end side.

The external diameter of the sheath 10 is formed so as to be insertable through a channel (not shown) of an endoscope. Additionally, the sheath 10 has flexibility and electrical insulation.

The sheath 10 has a closely wound coil 11, an insulating tube 12 that covers an outer peripheral surface of the closely wound coil 11, and a stopper member 13 that is fixed to an inner peripheral surface of a distal end portion of the closely wound coil 11.

The closely wound coil 11 is constituted, for example, by winding a plate-shaped coil with no gap in the direction of an axis C1. The closely wound coil 11 has flexibility so that a shape of the closely wound coil 11 can be easily changed in accordance with shape changes in an insertion section of the endoscope in a state where the sheath 10 is inserted into the channel of the endoscope.

The insulating tube 12 is formed from, for example, a resin material having heat resistance or flexibility, such as a tetrafluoroethylene material. The external diameter of the insulating tube 12 is formed with an external diameter so that the insulating tube is insertable through the channel of the endoscope.

The stopper member 13 is formed in a tubular shape from a material having insulation. A thick portion 13a is formed at a distal end portion of the stopper member 13. The thickness of the thick portion 13a is thicker inward in the radial direction of the sheath 10 than the thickness of a proximal end portion of the stopper member 13.

An inner peripheral surface and an outer peripheral surface of a coupling portion between the closely wound coil 11 and the stopper member 13 are formed so as to be almost flush with each other.

The aforementioned insulated tip 15 that is formed in a tubular shape is fixed to the inner peripheral surface of the insulating tube 12 located further toward the distal end side than the thick portion 13a. The insulated tip 15 is fixed to the insulating tube 12 and the stopper member 13 so that the tip of the insulated tip 15 and the tip of the insulating tube 12 coincide with each other in the axis direction C1 (are located on the same plane).

A tube hole 16 formed in the insulated tip 15 has a smaller-diameter hole portion 16a that is formed on the proximal end side in the insulated tip 15 and reaches a proximal end surface of the insulated tip 15, a middle-diameter hole portion 16b that has a larger internal diameter than the smaller-diameter hole portion 16a in the distal end side of the smaller-diameter hole portion 16a, and a larger-diameter hole portion 16c that has a larger internal diameter than the middle-diameter hole portion 16b in the distal end side of the middle-diameter hole portion 16b. The smaller-diameter hole portion 16a and the middle-diameter hole portion 16b communicate with each other, and the middle-diameter hole portion 16b and the larger-diameter hole portion 16c communicate with each other.

It is preferable that the insulated tip 15 be formed from a material having heat resistance and electrical insulation, such as a zirconia or ceramic material. An inner peripheral surface of the smaller-diameter hole portion 16a is formed so as to be substantially flush with an inner peripheral surface of the thick portion 13a.

A liquid-supply port 17 in which an injection port 17a communicating with the conduit line 10a of the sheath 10 is formed is attached to a proximal end portion of the sheath 10. A syringe (liquid-supply means) D is attachable to and detachable from the injection port 17a. A saline (fluid) is stored in a syringe body D1 of the syringe D.

The saline can be supplied to the conduit line 10a through the injection port 17a by pushing the plunger D2 into the syringe body D1 to supply the liquid, in a state where the syringe body D1 is attached to the injection port 17a.

Metal having conductivity can be suitable used for the operating wire 20.

Figure 2:
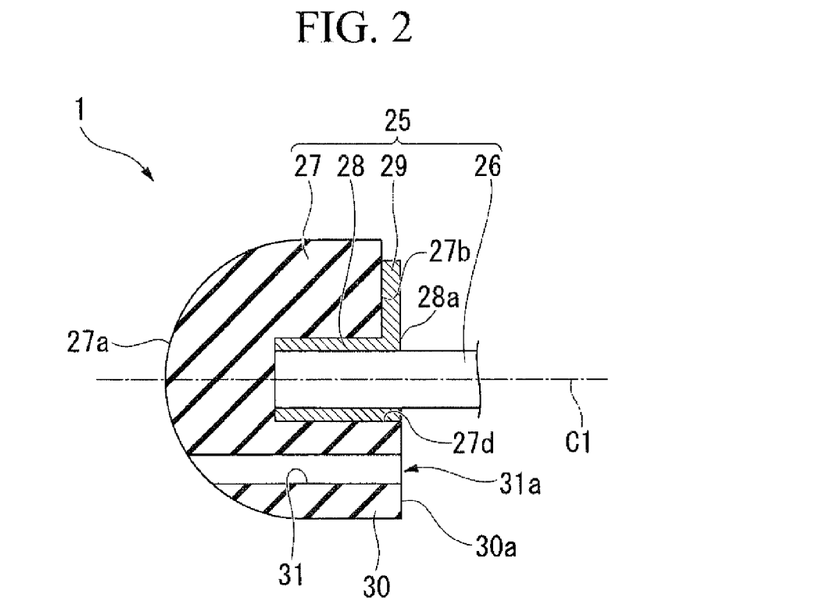
FIG. 2 is a cross-sectional view of a side surface of an electrode portion of the high-frequency knife.
Figure 3:
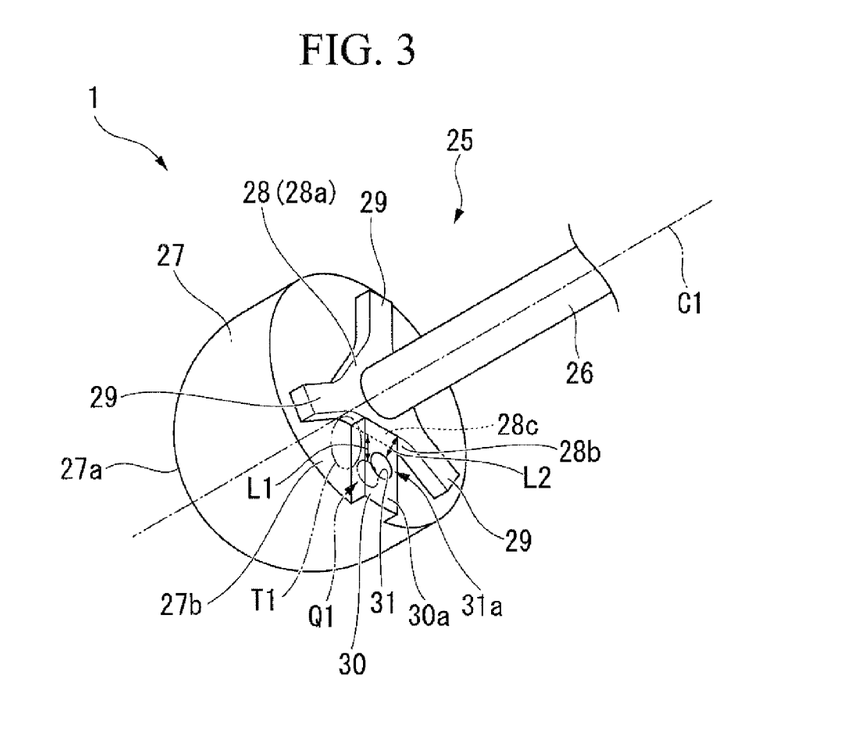
FIG. 3 is a perspective view of the electrode portion.

The electrode portion 25, as shown in FIGS. 1 to 3, has a rod-shaped electrode 26, a larger-diameter portion 27, a tubular electrode 28, and an auxiliary electrode 29. The electrode 26 extends in the axis direction C1, and a proximal end portion of the electrode 26 is electrically connected to the distal end portion of the operating wire 20. The larger-diameter portion 27 is provided at the distal end portion of the electrode 26. The electrode 28 is formed in a tubular shape that extends in the axis direction so as to surround the electrode 26. Three auxiliary electrodes 29 extend in the radial direction from an outer peripheral surface of the tubular electrode 28.

The rod-shaped electrode (a first electrode) 26 is formed from metal, such as stainless steel having biocompatibility and conductivity. The rod-shaped electrode 26, as shown in FIG. 1, is advanceably and retractably inserted through the tube hole 16 and the stopper member 13. The external diameter of the rod-shaped electrode 26 is set so that a gap S is formed between the smaller-diameter hole portion 16a and the rod-shaped electrode 26 and between the stopper member 13 and the rod-shaped electrode 26. A stopper receiving portion 21 formed in a tubular shape from a material having conductivity is attached to an outer peripheral surface of a connecting portion between the rod-shaped electrode 26 and the operating wire 20. The external diameter of the stopper receiving portion 21 is set to be greater than the internal diameter of the thick portion 13a.

As will be described below, an inclination portion 21a is formed on an outer peripheral surface of a distal end portion of the stopper receiving portion 21 so that the conduit line 10a is not sealed within the sheath 10 when the stopper receiving portion 21 is made to abut against the stopper member 13.

The larger-diameter portion 27 is formed in a substantially columnar shape. The larger-diameter portion 27 has a larger external diameter than the rod-shaped electrode 26, and is formed to be approximately equal to the internal diameter of the sheath 10.

The larger-diameter portion 27, as shown in FIGS. 2 and 3, has a tip surface 27a that is formed in the shape of a curved surface that becomes convex toward the distal end side, and has a proximal end surface 27b that is flatly formed so as to be orthogonal to the axis direction C1.

A protruding portion (distance increasing portion) 30 is provided on the proximal end surface 27b of the larger-diameter portion 27 so as to protrude toward the proximal end side. That is, the protruding portion 30 constitutes a portion of the larger-diameter portion 27. The protruding portion 30 is formed in the shape of a substantially rectangular parallelepiped, and extends from the outer peripheral surface of the tubular electrode (the second electrode) 28 to the edge of the proximal end surface 27b.

An attachment hole 27d that extends in the axis direction C1 is formed at the center of the proximal end surface 27b of the larger-diameter portion 27. Additionally, the larger-diameter portion 27 is formed with one guide hole (through hole) 31 that extends in the axis direction C1 and passes through the larger-diameter portion 27 and the protruding portion 30. That is, an opening 31a of the guide hole 31 on the proximal end side is formed in a proximal end surface 30a of the protruding portion 30 that protrudes to the proximal end side. The guide hole 31 is formed at a position on the radial outer side of the hole 27d when being viewed in the axis direction C1.

The larger-diameter portion 27 is formed together with the protruding portion 30 from the same material as the stopper member 13 having electrical insulation.

In this example, the tubular electrode 28 is formed so as to extend to the distal end side and proximal end side from the proximal end surface 27b of the larger-diameter portion 27. A distal end portion in the tubular electrode 28 is arranged within the attachment hole 27d of the larger-diameter portion 27, and is fixed to the larger-diameter portion 27. The tubular electrode 28 is formed so that a proximal end surface 28a of the tubular electrode 28 coincides with the proximal end surface 30a of the protruding portion 30 (is located on the same plane) in the axis direction C1.

The distal end portion of the rod-shaped electrode 26 is inserted through the tubular electrode 28. The tubular electrode 28 and the tubular rod-shaped electrode 26 are connected together by welding or the like.

The respective auxiliary electrodes 29 are formed in the shape of a substantially rectangular parallelepiped, and are provided at the proximal end surface 27b of the larger-diameter portion 27. The respective auxiliary electrodes 29 are radially arranged at approximately equal intervals in the circumferential direction of the sheath 10. The cross-sections of the respective auxiliary electrodes 29 by planes orthogonal to the radial direction in which the auxiliary electrodes 29 extend from the axis C1 are formed in a rectangular shape.

The respective auxiliary electrodes 29 are formed so that the guide hole 31 is arranged between the auxiliary electrodes 29 adjacent to each other in the circumferential direction when viewed in the axis direction C1.

The length from the axis C1 to the tips of the respective auxiliary electrodes 29 that extend in the radial direction is set so as to be slightly smaller than the radius of the larger-diameter hole portion 16c.

The respective auxiliary electrodes 29 are formed integrally with the aforementioned tubular electrode 28 from conductive metal, such as a titanium alloy. The respective auxiliary electrodes 29 and the tubular electrode 28 are electrically connected to the rod-shaped electrode 26.

In the electrode portion 25 configured in this way, as shown in FIG. 3, the protruding portion 30 increases a creeping distance along an external surface of the larger-diameter portion 27 between an outer peripheral surface 28b of the tubular electrode 28 exposed to the outside and the opening 31a of the guide hole 31. The creeping distance means a minimum distance among distances along the external surface of the larger-diameter portion 27 between the aforementioned outer peripheral surface 28b and the opening 31a.

When the larger-diameter portion 27 is not provided with the protruding portion 30, the opening of the guide hole 31 on the proximal end side is arranged at a position Q1, and an outer peripheral surface 28c is exposed to the outside. In this case, the creeping distance along the external surface of the larger-diameter portion 27 between the outer peripheral surface exposed to the outside and the opening 31a is L1. In contrast, when the protruding portion 30 is provided at the larger-diameter portion 27 as in the present embodiment, the outer peripheral surface 28c is covered and is not exposed to the outside. Therefore, the creeping distance along the external surface of the larger-diameter portion 27 between the outer peripheral surface 28b and the opening 31a is L2.

In this way, the creeping distance increases from L1 to L2 by providing the larger-diameter portion 27 with the protruding portion 30.

The high-frequency knife 1 of the present embodiment, as shown in FIG. 1, includes an operating section 35 provided on the proximal end side of the liquid-supply port 17.

The operating section 35 includes an operating section body 36 that is fixed to a proximal end portion of the liquid-supply port 17, and a slider 37 for operation that is slidable with respect to the operating section body 36. A guide shaft portion 36b is formed along the axis C1 at the operating section body 36. The slider 37 for operation is slidable along the axis C1. The operating section body 36 has a finger-hooking ring 36a at a proximal end portion thereof.

The slider 37 for operation includes finger-hooking rings 37a and 37b side by side in a direction orthogonal to the axis C1. For this reason, the slider 37 for operation can be made to slide in the axis direction C1 with respect to the operating section body 36, for example, by putting an operator's thumb into the ring 36a of the operating section body 36, putting operator's index finger and middle finger into the rings 37a and 37b of the slider 37 for operation, and operating the rings with the operator's thumb, index finger, and middle finger.

A proximal end side of the aforementioned operating wire 20 is inserted through the liquid-supply port 17 and the operating section body 36, and a proximal end portion of the operating wire 20 is fixed to the slider 37 for operation. Sealant (not shown) for sealing the conduit line and the operating wire 20 between the liquid-supply port 17 and the operating section body 36 is provided within the liquid-supply port 17.

The slider 37 for operation includes a connection connector 38 to which a cord that leads to a high frequency generator (not shown) is electrically connected.

The connection connector 38 is electrically connected to the proximal end side of the operating wire 20.

In the high-frequency knife 1 configured in this way, as shown in FIG. 1, if the operating wire 20 is pushed into the distal end side with respect to the sheath 10 by moving the slider 37 for operation to the distal end side with respect to the operating section body 36, a push-in state where the operating wire 20 is pushed into the distal end side is positioned as the stopper receiving portion 21 abuts against the stopper member 13. In this push-in state, the larger-diameter portion 27 and the respective auxiliary electrodes 29 are separated to the distal end side with respect to the insulated tip 15, and the rod-shaped electrode 26 and the respective auxiliary electrodes 29 are exposed to the outside.

Figure 4:
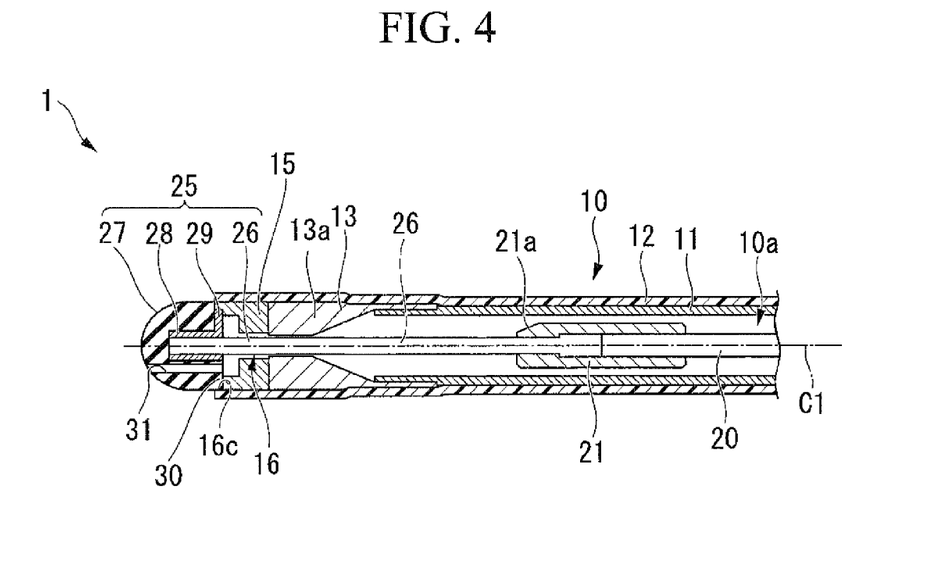
FIG. 4 is a cross-sectional view of a side surface of an electrode portion of the high-frequency knife.

On the other hand, if the operating wire 20 is pulled back to the proximal end side with respect to the sheath 10 by moving the slider 37 for operation to the proximal end side with respect to the operating section body 36, as shown in FIG. 4, the respective auxiliary electrodes 29 and the protruding portion 30 are accommodated within the larger-diameter hole portion 16c, and the larger-diameter portion 27 abuts against the tip surface of the insulated tip 15. Accordingly, the pull-back state where the operating wire 20 is pulled back to the proximal end side is positioned.

In this pull-back state, the high-frequency knife 1 is configured as follows. That is, the rod-shaped electrode 26 and the respective auxiliary electrodes 29 are brought into a state where these electrodes are accommodated within the sheath 10 and are not exposed to the outside. Accordingly, the tube hole 16 and the guide hole 31 communicate with each other.

Next, the operation of the high-frequency knife 1 configured as mentioned above is described. In the following, the operation when excision of a mucous membrane within a body cavity is endoscopically performed using the high-frequency knife 1 is described.

First, although not shown, an injection needle is endoscopically introduced into the body cavity through the channel of the endoscope. At this time, the injection needle is introduced, observing an image, which is acquired by an observation unit of the endoscope, with a display unit, such as a monitor.

Figure 5:
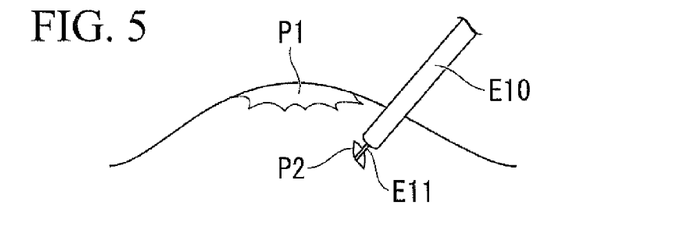
FIG. 5 is a view illustrating a procedure using the high-frequency knife and is a view showing a state when a hole is made in a portion of a mucous membrane.

Using the injection needle, as shown in FIG. 5, a saline is injected into a submucosal layer of a lesioned mucous membrane portion P1 that is a target part of the body cavity to be excised, and the lesioned mucous membrane portion P1 is caused to bulge.

Next, a counter electrode plate (not shown) is worn by a patient. Thereafter, a high-frequency knife E10 having a needlelike electrode (knife portion) E11 is endoscopically introduced similarly as in the related art. The initial incision of applying an electric current to the electrode E11 to make a hole P2 in a portion of the mucous membrane around the lesioned mucous membrane portion P1 is performed. Then, the high-frequency knife E10 is pulled out and removed from the channel of the endoscope.

Figure 6:
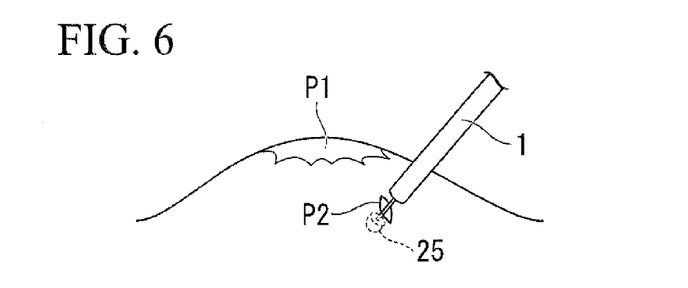
FIG. 6 is a view illustrating the procedure using the high-frequency knife and is a view showing a state where the electrode portion is inserted into the hole of the mucous membrane.

Subsequently, the high-frequency knife 1 of the present embodiment brought into the pull-back state is introduced into the body cavity via an empty channel of the endoscope. The distal end portion of the high-frequency knife 1 is made to protrude from the tip of the insertion section of the endoscope. Then, the operator or a helper puts his/her fingers into the rings 36a, 37a, and 37b pushes the slider 37 for operation into the distal end side with respect to the operating section body 36, and brings the high-frequency knife 1 into a push-in state. As shown in FIG. 6, the electrode portion 25 of the high-frequency knife 1 is inserted from the distal end side into the hole P2 that is initially incised.

Figure 7:
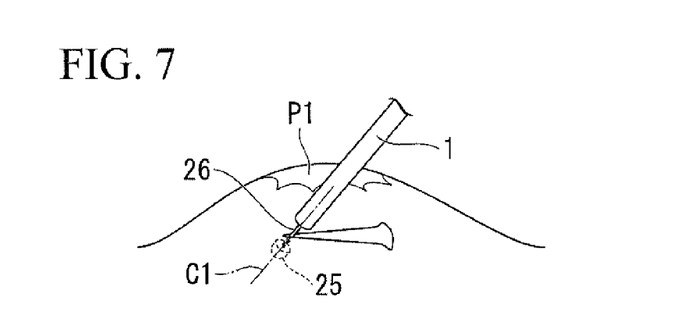
FIG. 7 is a view illustrating the procedure using the high-frequency knife and is a view showing a state where the electrode portion is moved in a transverse direction to perform incision.

Next, the high frequency generator (not shown) is connected to the connection connector 38 of the operating section 35. While a high-frequency voltage is applied to the rod-shaped electrode 26 and the auxiliary electrodes 29 via the connection connector 38 and the operating wire 20 by the high frequency generator, as shown in FIG. 7, the electrode portion 25 of the high-frequency knife 1 is moved along a predetermined excision direction. For example, if the electrode portion 25 is moved in the transverse direction orthogonal to the axis C1, the mucous membrane coming into contact with the rod-shaped electrode 26, the tubular electrode 28, and the auxiliary electrode 29 is incised.

The rod-shaped electrode 26 or the like becomes high in temperature by applying the high-frequency voltage, and the burnt mucous membrane sticks to the outer peripheral surface 28b of the tubular electrode 28. In this case, as shown in FIG. 3, since the burnt mucous membrane T1 sticks between the protruding portion 30 and an auxiliary electrode 29, the guide hole 31 is kept from being blocked.

Figure 8:
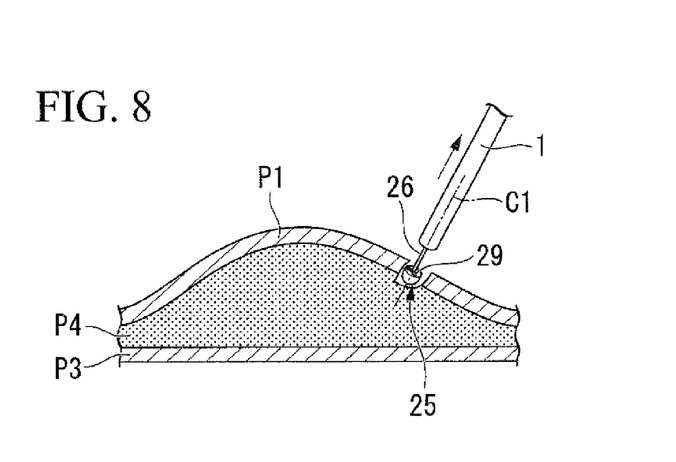
FIG. 8 is a view illustrating the procedure using the high-frequency knife and is a view showing a state where the electrode portion is moved in a longitudinal direction to perform incision.

When it is difficult to move the electrode portion 25 in the transverse direction, as shown in FIG. 8, the electrode portion 25 is moved in the longitudinal direction that is the axis direction C1. Then, the mucous membrane hooked by the auxiliary electrode 29 is incised by coming into contact with the proximal end surface of the auxiliary electrode 29.

The electrode portion 25 of the high-frequency knife 1 is moved combining this movement in the longitudinal direction and the aforementioned movement in the transverse direction. Then, the periphery of the lesioned mucous membrane portion P1 is incised over the circumferential direction of the lesioned mucous membrane portion P1.

In the present embodiment, the larger-diameter portion 27 is formed from a material having insulation. For this reason, even if the tip surface 27a of the larger-diameter portion 27 comes into contact with a non-excised tissue P3, such as a muscle layer, by the movement of the larger-diameter portion 27 in the longitudinal direction, the rod-shaped electrode 26 and the respective auxiliary electrodes 29 to which the high-frequency voltage is applied do not act on the non-excised tissue P3. Accordingly, the operator does not need to perform the complicated operation of moving the rod-shaped electrode 26 at a constant depth so that the non-excised tissue P3 located at a deep portion of a part to be excised, and the rod-shaped electrode 26 do not come into contact with each other.

Symbol P4 in FIG. 8 represents the submucosal layer between the lesioned mucous membrane portion P1 and the non-excised tissue P3.

When the lesioned mucous membrane portion P1 is completely incised over the circumferential direction as mentioned above, as shown in FIG. 9, the rod-shaped electrode 26 and/or the respective auxiliary electrodes 29 are made to abut against an opening P6 obtained by incising the periphery of the lesioned mucous membrane portion P1, the lesioned mucous membrane portion P1 is sequentially incised combining the movement of the high-frequency knife 1 in the transverse direction and the longitudinal direction, and the lesioned mucous membrane portion P1 is peeled off.

Figure 9:
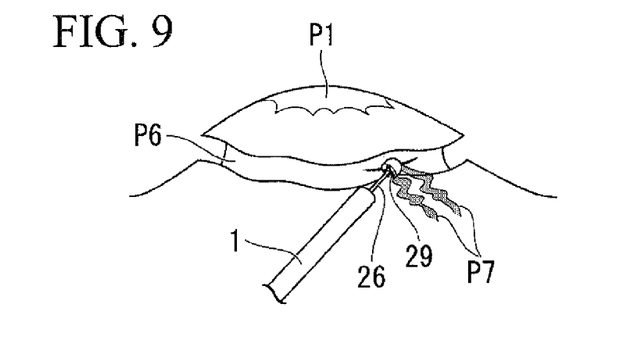
FIG. 9 is a view illustrating the procedure using the high-frequency knife and is a view showing a state where blood has flowed out of an opening of a tissue.

When the lesioned mucous membrane portion P1 is incised, blood P7 may flow out.

Figure 10:
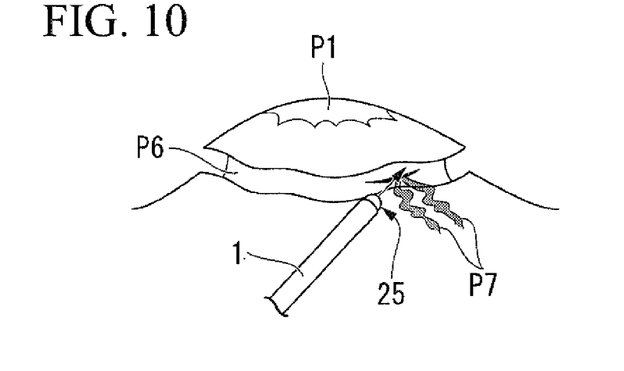
FIG. 10 is a view illustrating the procedure using the high-frequency knife and is a view showing a state where the blood that has flowed out is washed out.

At this time, as shown in FIG. 10, the high-frequency knife 1 is brought into the pull-back state, and the syringe body D1 is attached to the injection port 17a of the liquid-supply port 17. If the plunger D2 is pushed in, the saline stored in the syringe body D1 is supplied through the liquid-supply port 17, the conduit line 10a, the tube hole 16, and the guide hole 31, and is jetted to the front of the larger-diameter portion 27. This cleanses the blood P7. A part from which the blood P7 has flowed out becomes clear, and it is easy to perform treatment of hemostasis.

The treatment of hemostasis is performed, for example, by inserting a treatment tool for coagulation (not shown) from the channel of the endoscope to coagulate the tissue of a bleeding portion.

Figure 11:
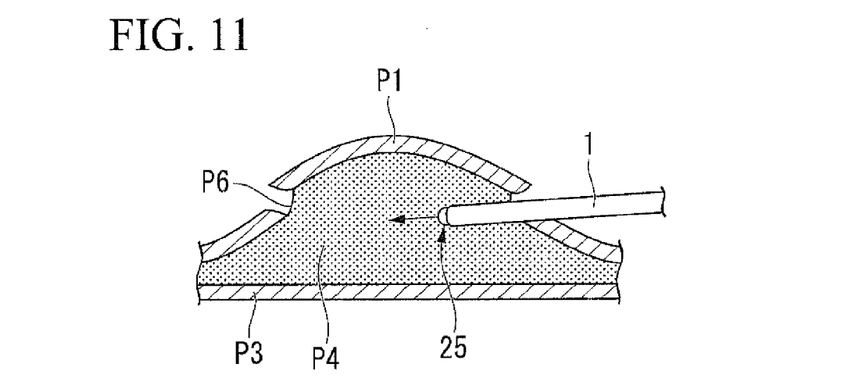
FIG. 11 is a view illustrating the procedure using the high-frequency knife and is a view showing a state where a saline is added and injected into a submucosal layer.

Additionally, if time passes since the injection of the saline by the aforementioned injection needle, the saline injected into the submucosal layer P4 of the lesioned mucous membrane portion P1 may move to a peripheral portion, and the height at which the lesioned mucous membrane portion P1 bulges may become low. At this time, as shown in FIG. 11, the electrode portion 25 of the high-frequency knife 1 brought into the pull-back state is introduced into the submucosal layer P4 through the opening P6. The lesioned mucous membrane portion P1 is caused to bulge again by pushing in the plunger D2 and injecting the saline into the submucosal layer P4.

Then, the high-frequency knife 1 is returned to the push-in state, and the lesioned mucous membrane portion P1 is completely incised and peeled off. The high-frequency knife 1 is brought into the push-back state, and is pulled out from the inside of the channel of the endoscope to the hand side. Grip forceps (not shown) or the like is inserted through an empty channel of the endoscope. The grip forceps are operated to take out the lesioned mucous membrane portion P1 endoscopically, and a series of treatment is completed.

As described above, according to the high-frequency knife 1 of the present embodiment, a tissue coming into contact with the rod-shaped electrode 26 or the like can be incised by bringing the high-frequency knife 1 into the push-in state and applying a high-frequency voltage to the electrode portion 25 via the operating wire 20. On the other hand, the saline can be jetted to the front of the larger-diameter portion 27 through the tube hole 16 of the insulated tip 15 and the guide hole 31 of the larger-diameter portion 27 by bringing the high-frequency knife 1 into the pull-back state and supplying the saline to the conduit line 10a of the sheath 10 by the syringe D.

When a tissue is incised, a burnt tissue sticks to the outer peripheral surface 28b of the tubular electrode 28. However, since the larger-diameter portion 27 is provided with the protruding portion 30, the creeping distance along the external surface of the larger-diameter portion 27 between the outer peripheral surface 28b of the tubular electrode 28 exposed to the outside and the opening 31a of the guide hole 31 increases. For this reason, the distance until the burnt tissue that has stuck to the outer peripheral surface 28b of the tubular electrode 28 reaches the opening 31a of the guide hole 31 along the external surface of the larger-diameter portion 27 becomes long. Accordingly, the guide hole 31 can be kept from being blocked by the burnt tissue that has stuck to the outer peripheral surface 28b.

Additionally, since the protruding portion 30 is formed from the material having insulation, the burnt tissue does not easily stick to the protruding portion 30. Accordingly, the burnt tissue on the protruding portion 30 can be easily removed.

The proximal end surface 28a of the tubular electrode 28 and the proximal end surface 30a of the protruding portion 30 are formed so as to coincide with each other (be located on the same plane) in the axis direction C1. When the high-frequency knife 1 is brought into the push-in state and the electrode portion 25 is moved in the transverse direction, a tissue can be smoothly moved between the proximal end surface 28a of the tubular electrode 28 and the proximal end surface 30a of the protruding portion 30.

The electrode portion 25 has the three auxiliary electrodes 29, and when viewed in the axis direction C1, the guide hole 31 is arranged between the auxiliary electrodes 29 that are adjacent to each other in the circumferential direction. Accordingly, the incision using the auxiliary electrodes 29 can be easily performed by making the occupation area of the auxiliary electrodes 29 large when viewed in the axis direction C1, and the external diameter of the larger-diameter portion 27 can be kept from becoming large by forming the guide hole 31.

The configuration of the electrode portion 25 in the high-frequency knife 1 of the present embodiment can be variously modified as will be described below.

Figure 12:
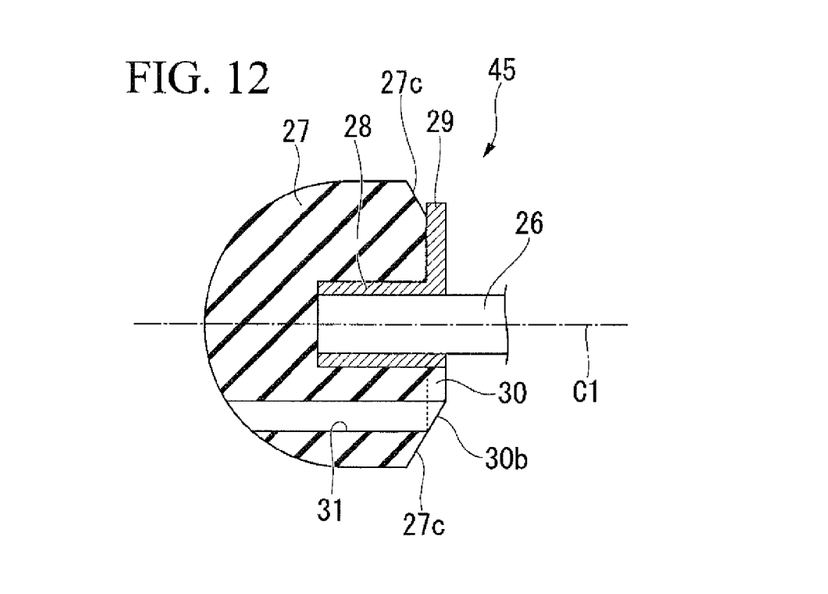
FIG. 12 is a cross-sectional view of a side surface of an electrode portion of a high-frequency knife of a modification example in the embodiment of the invention.

For example, in an electrode portion 45 shown in FIG. 12, a chamfered portion 27c and a chamfered portion 30b that decrease in diameter toward the proximal end side may be respectively formed at an outer peripheral surface of a proximal end portion of the larger-diameter portion 27 and at an outer peripheral surface of the protruding portion 30.

By adopting such a configuration, an angled portion in the proximal end portion of the electrode portion 45 decreases, and the electrode portion 45 can be smoothly moved toward the proximal end side within the body or the like.

Figure 13:
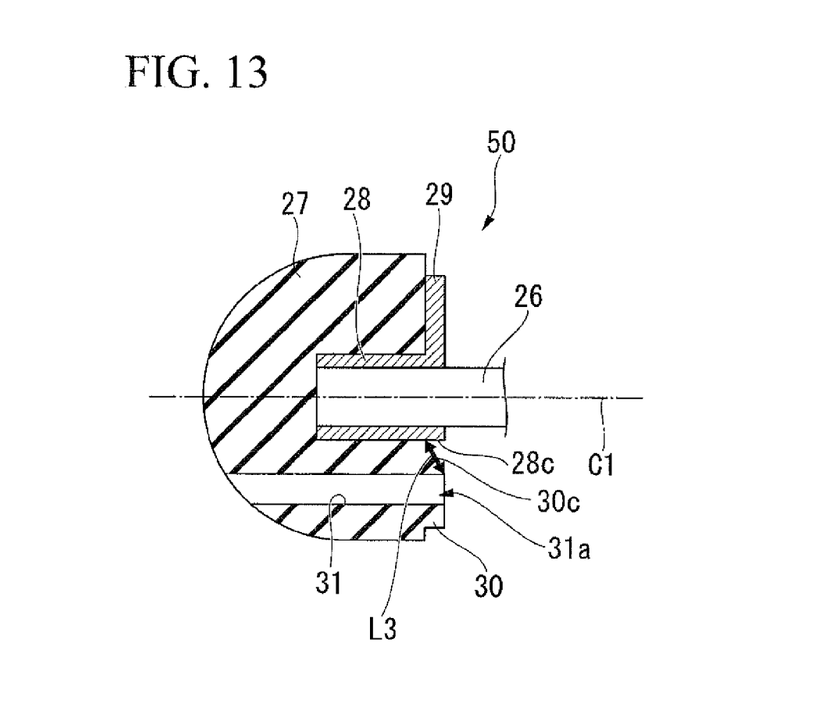
FIG. 13 is a cross-sectional view of a side surface of an electrode portion of a high-frequency knife of a modification example in the embodiment of the invention.

In an electrode portion 50 shown in FIG. 13, the part of the protruding portion 30 adjacent to the tubular electrode 28 may be formed with a groove portion 30c recessed toward the distal end side.

In this case, the creeping distance along the external surface of the larger-diameter portion 27 between the outer peripheral surface 28c exposed to the outside and the opening 31a of the guide hole 31 is L3. Also, since the burnt mucous membrane that has stuck to the outer peripheral surface 28c of the tubular electrode 28 is first accumulated in the groove portion 30c, the guide hole 31 can be kept from being blocked with the burnt mucous membrane that has stuck.

Figure 14:
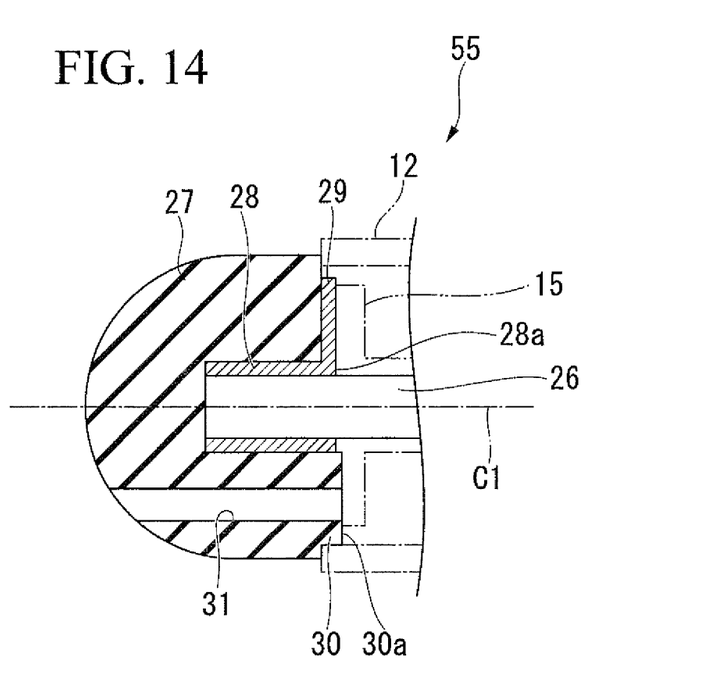
FIG. 14 is a cross-sectional view of a side surface of an electrode portion of a high-frequency knife of a modification example in the embodiment of the invention.

In an electrode portion 55 shown in FIG. 14, the electrode portion may be configured so that the proximal end surface 30a of the protruding portion 30 is arranged further toward the proximal end side than the proximal end surface 28a of the tubular electrode 28 in the axis direction C1. In this case, it is preferable to form the insulated tip 15 according to the shape of the protruding portion 30 so as to be recessed toward the proximal end side.

Figure 15:
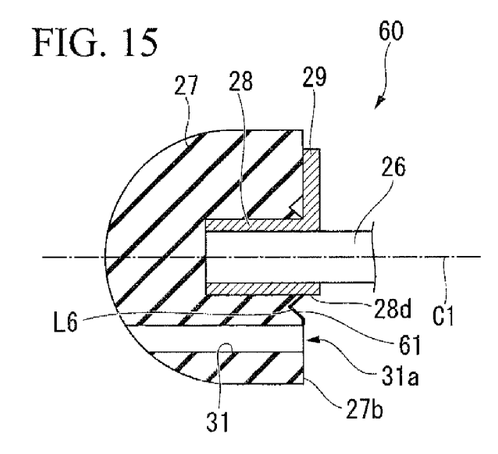
FIG. 15 is a cross-sectional view of a side surface of an electrode portion of a high-frequency knife of a modification example in the embodiment of the invention.
Figure 16:
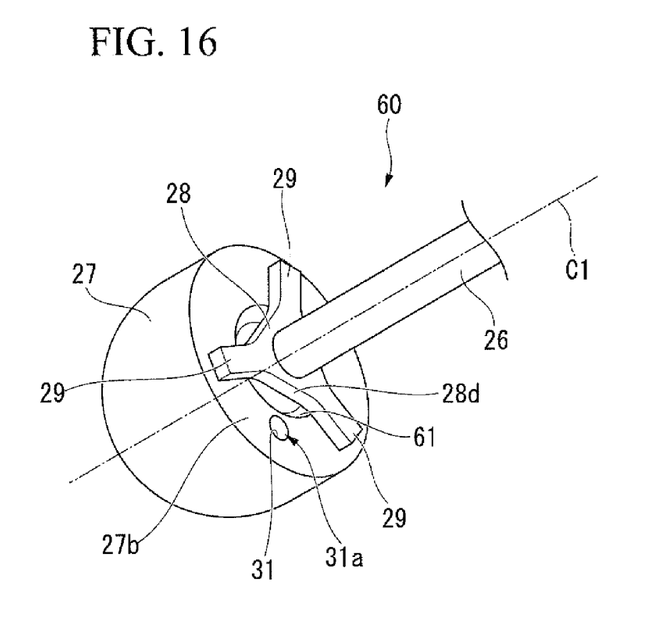
FIG. 16 is a perspective view of the electrode portion.

In an electrode portion 60 shown in FIGS. 15 and 16, instead of the protruding portion 30 of the aforementioned embodiment, a groove portion (distance increasing portion) 61 formed so as to be recessed from the proximal end surface 27b of the larger-diameter portion 27 toward the distal end side may be provided. The groove portion 61 is formed over the entire circumference around the axis C1 at a position between the tubular electrode 28 and the openings 31a of the guide hole 31 when viewed in the axis direction C1. The groove portion 61 is formed in a triangular shape that becomes narrows toward the distal end side, in a cross-section orthogonal to the circumferential direction.

In this case, the creeping distance along the external surface of the larger-diameter portion 27 between an outer peripheral surface 28d of the tubular electrode 28 exposed to the outside and the opening 31a of the guide hole 31 is the length of a thick line L6. Since the burnt mucous membrane that has stuck to the outer peripheral surface 28d of the tubular electrode 28 is first accumulated in the groove portion 61, the guide hole 31 can be kept from being blocked with the burnt mucous membrane that has stuck.

Although the groove portion 61 is formed over the entire circumference around the axis C1 in the present modification example, the groove portion 61 may be formed only in the vicinity of the opening 31a of the guide hole 31.

Figure 17:
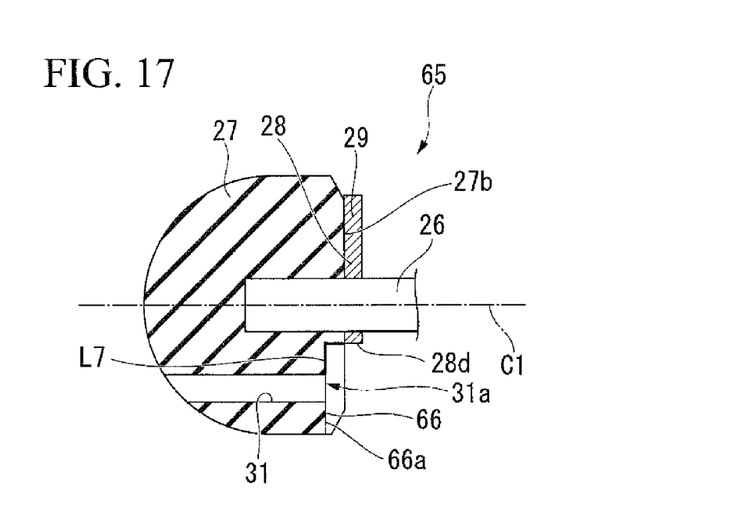
FIG. 17 is a cross-sectional view of a side surface of an electrode portion of a high-frequency knife of a modification example in the embodiment of the invention.
Figure 18:
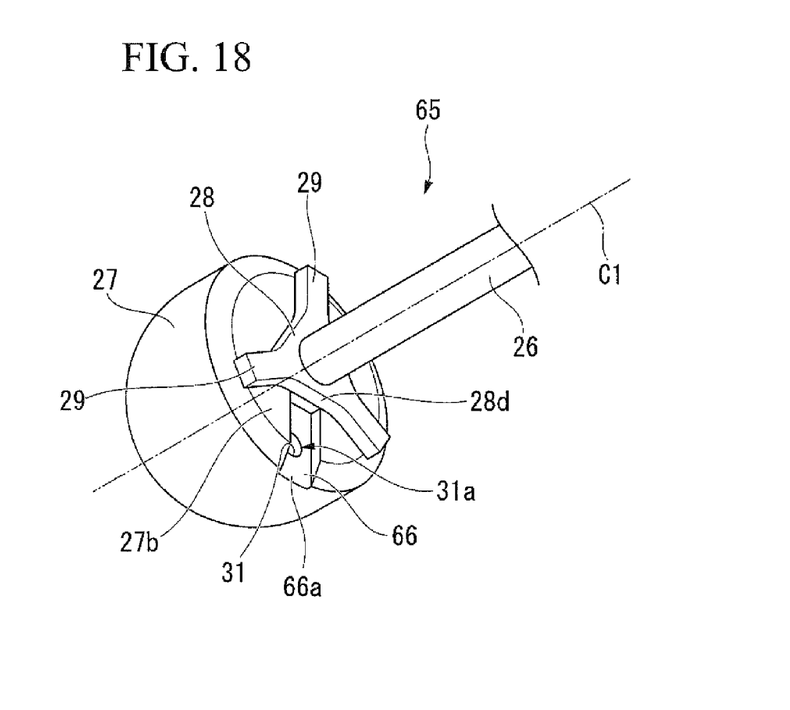
FIG. 18 is a perspective view of the electrode portion.

In an electrode portion 65 shown in FIGS. 17 and 18, instead of the protruding portion 30 of the aforementioned embodiment, a groove portion (distance increasing portion) 66 formed so as to be recessed from the proximal end surface 27b of the larger-diameter portion 27 toward the distal end side may be included. The groove portion 66 is formed in the shape of a rectangular parallelepiped, and is formed at a position that overlaps the opening 31a of the guide hole 31 when viewed in the axis direction C1.

In this modification example, the tubular electrode 28 is formed so as to extend from the proximal end surface 27b of the larger-diameter portion 27 only to the proximal end side. The opening 31a of the guide hole 31 is formed in a bottom surface 66a of the groove portion 66 recessed from the proximal end surface 27b toward the distal end side.

In this case, the creeping distance along the external surface of the larger-diameter portion 27 between the outer peripheral surface 28d of the tubular electrode 28 exposed to the outside and the opening 31a of the guide hole 31 is the length of a thick line L7. Also, since the burnt mucous membrane that has stuck to the outer peripheral surface 28d of the tubular electrode 28 is accumulated in the groove portion 66, the guide hole 31 can be kept from being blocked with the burnt mucous membrane that has stuck.

Figure 19:
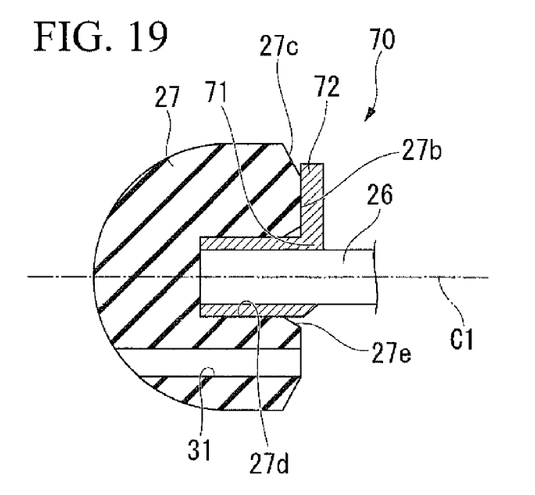
FIG. 19 is a cross-sectional view of a side surface of an electrode portion of a high-frequency knife of a modification example in the embodiment of the invention.
Figure 20:
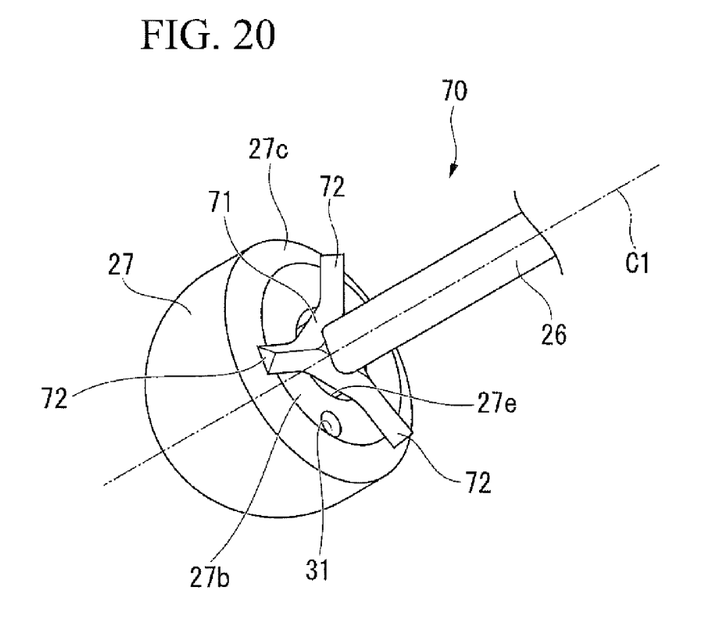
FIG. 20 is a perspective view of the electrode portion.

In an electrode portion 70 shown in FIGS. 19 and 20, instead of the tubular electrode 28, the auxiliary electrodes 29, and the protruding portion 30 of the embodiment, a tubular electrode 71 and an auxiliary electrode 72 may be included.

The tubular electrode 71 is formed so as to decrease in diameter to the proximal end side.

In this modification example, the electrode portion 70 has three auxiliary electrodes 72. The cross-sections of the respective auxiliary electrodes 72 by planes orthogonal to the radial direction in which the auxiliary electrodes 72 extend from the axis C1 are formed in a triangular shape that becomes narrows toward the proximal end side. That is, the surfaces of the auxiliary electrodes 72 exposed to the outside are configured so as to be directed to the proximal end side.

A groove portion 27e recessed toward the distal end side is formed in the portion of the proximal end surface 27b of the larger-diameter portion 27 that is adjacent to the attachment hole 27d.

If a high-frequency voltage is applied to the rod-shaped electrode 26 and the auxiliary electrodes 72 of the electrode portion 70 that is configured in this way, the burnt mucous membrane that has stuck to the auxiliary electrodes 72 sticks to the surfaces of the auxiliary electrodes 72 exposed to the outside, and is accumulated toward the proximal end side. For this reason, the accumulated burnt mucous membrane can be kept from clogging the guide hole 31.

Although the embodiment of the invention has been described above in detail with reference to the drawings, specific configuration is not limited to this embodiment, and changes of the configuration are also included without departing from the scope of the invention.

For example, although the electrode portion includes the three auxiliary electrodes in the aforementioned embodiment and modification examples, the number of auxiliary electrodes included in the electrode portion is not limited, and may be one or two, or may be four or more.

The number of guide holes 31 formed in the larger-diameter portion 27 is also not limited to one, and may be two or more.

Additionally, in the aforementioned embodiment and modification examples using the electrode portions 45, 50, 55, 60, and 70, the tubular electrode 28 may be formed so as to extend to the tip and proximal end side from the proximal end surface 27b of the larger-diameter portion 27. However, the tubular electrode 28 may be formed so as to extend from the proximal end surface 27b only to the proximal end side.

Although the preferred examples of the invention have been described above, the invention is not limited to these examples. Additions, omissions, substitutions, and other modifications can be made without departing from the concept of the present invention. The invention is not to be considered as being limited by the foregoing description, and is limited only by the scope of the appended claims.

The invention claimed is:

1. A high-frequency knife comprising:
   a sheath which has electric insulation and flexibility, has a conduit line formed therein and extends in an axis direction,
   an operating wire which is inserted through the conduit line so as to be capable of advancing and retracting in the axis direction; and
   an electrode portion which is provided at a distal end portion of the operating wire,
   wherein the electrode portion includes:
   a first electrode which is rod-shaped, extends in the axis direction, and has a proximal end portion electrically connected to the operating wire;
   a second electrode which is electrically connected to a distal end of the first electrode and is formed so as to surround the distal end of the first electrode; and
   a larger-diameter portion which is provided at the distal end portion of the first electrode, has electric insulation, and has a larger external diameter than an external diameter of the first electrode,
   wherein a protruding portion is provided on a proximal end of the larger-diameter portion so as to protrude toward a proximal end portion of the first electrode,
   the second electrode is formed so that a proximal end surface of the second electrode coincides with the proximal end surface of the protruding portion,
   a larger-diameter portion has a through hole that extends in the axis direction, and
   an opening that communicates with the through hole is formed on the proximal end surface of the protruding portion.

2. The high-frequency knife according to claim 1,
   wherein the electrode portion has a plurality of auxiliary electrodes that extend radially outward from the outer peripheral surface of the second electrode, and
   wherein when viewed in the axis direction, the through hole of the larger-diameter portion is formed between the auxiliary electrodes that are adjacent to each other around an axis.

* * * * *